US009422211B2

(12) United States Patent
Takahashi et al.

(10) Patent No.: US 9,422,211 B2
(45) Date of Patent: Aug. 23, 2016

(54) PROCESS FOR PRODUCING 2,3,3,3-TETRAFLUOROPROPENE

(71) Applicant: DAIKIN INDUSTRIES, LTD., Osaka (JP)

(72) Inventors: Kazuhiro Takahashi, Osaka (JP); Hitoshi Motoyama, Osaka (JP); Takehiro Chaki, Osaka (JP); Daisuke Karube, Osaka (JP); Masayuki Kishimoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/408,339

(22) PCT Filed: Aug. 7, 2013

(86) PCT No.: PCT/JP2013/071897
§ 371 (c)(1),
(2) Date: Dec. 16, 2014

(87) PCT Pub. No.: WO2014/025065
PCT Pub. Date: Feb. 13, 2014

(65) Prior Publication Data
US 2015/0203421 A1    Jul. 23, 2015

Related U.S. Application Data

(60) Provisional application No. 61/680,768, filed on Aug. 8, 2012.

(30) Foreign Application Priority Data

Jun. 4, 2013 (JP) .................................. 2013-117657

(51) Int. Cl.
C07C 17/25 (2006.01)
C07C 17/20 (2006.01)

(52) U.S. Cl.
CPC ............. *C07C 17/20* (2013.01); *C07C 17/206* (2013.01); *C07C 17/25* (2013.01); *Y02P 20/582* (2015.11)

(58) Field of Classification Search
CPC .......................... C07C 17/25; C07C 17/206
See application file for complete search history.

(56) References Cited

U.S. PATENT DOCUMENTS

2009/0240090 A1    9/2009  Merkel et al.
2011/0155942 A1*   6/2011  Pigamo ................. B01J 23/866
                                                       252/2
2011/0207975 A9    8/2011  Merkel et al.

FOREIGN PATENT DOCUMENTS

| FR | WO 2012052797 A1 * | 4/2012 | ........... C07C 17/206 |
| JP | 2009-227675 | 10/2009 | |
| WO | 2007/079431 | 7/2007 | |
| WO | 2013/088195 | 6/2013 | |

OTHER PUBLICATIONS

International Search Report issued Nov. 20, 2013 in International (PCT) Application No. PCT/JP2013/071897 along with the Written Opinion.

* cited by examiner

*Primary Examiner* — Jafar Parsa
*Assistant Examiner* — Medhanit Bahta
(74) *Attorney, Agent, or Firm* — Wenderoth, Lind & Ponack, L.L.P.

(57) ABSTRACT

The present invention provides a process for producing 2,3,3,3-tetrafluoropropene, comprising the steps of producing 2-chloro-3,3,3-trifluoropropene by reacting anhydrous hydrogen fluoride with a specific chlorine-containing compound in a gas phase in the presence of a fluorination catalyst while heating; and producing 2,3,3,3-tetrafluoropropene by reacting 2-chloro-3,3,3-trifluoropropene with anhydrous hydrogen fluoride in a gas phase in the presence of a fluorination catalyst while heating, the step of producing 2-chloro-3,3,3-trifluoropropene being performed after the step of producing 2,3,3,3-tetrafluoropropene. According to the process, 2,3,3,3-tetrafluoropropene can be produced with reduced energy and equipment costs in an economically advantageous manner.

10 Claims, 3 Drawing Sheets

PROCESS FOR PRODUCING 2,3,3,3-TETRAFLUOROPROPENE

TECHNICAL FIELD

The present invention relates to a process for producing 2,3,3,3-tetrafluoropropene.

BACKGROUND ART

In a process for producing a fluoropropene by fluorinating a halopropane or a halopropene as a starting material with hydrogen fluoride, the reactions proceed in the route as described below when 1,1,1,2,3-pentachloropropane is fluorinated in a gas phase.

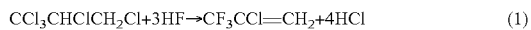

(1)

(2)

In these reactions, the reaction rate in the reaction for producing 2-chloro-3,3,3-trifluoropropene from 1,1,1,2,3-pentachloropropane (first reaction) is significantly different from that in the reaction for producing 2,3,3,3-tetrafluoropropene from 2-chloro-3,3,3-trifluoropropene (second reaction). Thus, it is inefficient to perform these reactions using a single reactor, and it is ideal to perform the reactions using separate reactors. For example, Patent Literature 1 listed below discloses a process in which fluorination is performed in a gas phase in three steps under conditions according to each reaction, using three reactors packed with different catalysts. Patent Literature 2 listed below discloses an integrated process using these reactions.

However, in these processes, it is difficult to obtain 100% conversion in each reaction, and it is necessary to separate the unreacted starting materials and the target product from the reaction mixture to recycle the unreacted starting materials. In such a case, the separation of the product from the reaction mixture is typically performed using a distillation column, and it is required to cool the reaction gas heated to several hundred degree Celsius and separate the unreacted starting materials using a distillation column. Thereafter, the product thus obtained are gasified by reheating and supplied to the next rector. Performing this operation in each of reaction steps results in significant energy loss. In addition, the number of distillation columns required for the separation is increased, leading to an increase in equipment costs.

CITATION LIST

Patent Literature

PTL 1: WO 2007/079431
PTL 2: JP2009-227675A

SUMMARY OF INVENTION

Technical Problem

The present invention has been accomplished in view of the state of the art described above, and its primary object is to provide a process for efficiently producing 2,3,3,3-tetrafluoropropene with reduced energy and equipment costs in an economically advantageous manner in a process comprising two-stage reaction steps in which 2,3,3,3-tetrafluoropropene is produced using at least one chlorine-containing compound selected from the group consisting of 1,1,1,2,3-pentachloropropane, 2,3-dichloro-1,1,1-trifluoropropane, and 1,1,2,3-tetrachloropropene as a starting material.

Solution to Problem

The present inventors conducted extensive investigations to achieve the above object and found the following fact. Specifically, when a reactor used in a trifluoropropene-producing reaction for producing 2-chloro-3,3,3-trifluoropropene, which is an intermediate product, from at least one chlorine-containing compound selected from the group consisting of 1,1,1,2,3-pentachloropropane, 2,3-dichloro-1,1,1-trifluoropropane, and 1,1,2,3-tetrachloropropene used as a starting material is disposed downstream of a reactor used in a tetrafluoropropene-producing reaction for producing the desired 2,3,3,3-tetrafluoropropene from 2-chloro-3,3,3-trifluoropropene, i.e., the reactors are disposed in a manner opposite to the conventional installation manner, the amount of hydrogen chloride generated in the tetrafluoropropene-producing reaction on the upstream side is less than the amount of hydrogen chloride generated in the trifluoropropene-producing reaction step, and thus the products of the tetrafluoropropene-producing reaction step can be supplied to the trifluoropropene-producing reaction step without removing hydrogen chloride. This eliminates the conventional need for a device for separating hydrogen chloride after the tetrafluoropropene-producing reaction step, thus enabling reduction in equipment costs.

In addition, the tetrafluoropropene-producing reaction for producing 2,3,3,3-tetrafluoropropene can be performed at a temperature higher than that in the trifluoropropene-producing reaction for producing 2-chloro-3,3,3-trifluoropropene from the starting materials. Thus, when the reactor used in the tetrafluoropropene-producing reaction is disposed upstream of the reactor used in the trifluoropropene-producing reaction, and the tetrafluoropropene-producing reaction is performed at a temperature higher than that in the trifluoropropene-producing reaction, heating energy required for the trifluoropropene-producing reaction can be saved or reduced by effectively using thermal energy of the tetrafluoropropene-producing reaction.

In particular, setting the reaction temperature in the trifluoropropene-producing reaction to a sufficiently low temperature compared to that in the tetrafluoropropene-producing reaction is highly advantageous in terms of energy costs. In such a case, the yield of the desired 2,3,3,3-tetrafluoropropene tends to decrease; however, the yield of 2,3,3,3-tetrafluoropropene can be improved by providing a small-scale region for reheating the products of the trifluoropropene-producing reaction and reheating the products. This enables 2,3,3,3-tetrafluoropropene to be produced in a high yield with reduced total energy costs. Such a production process is highly advantageous from an industrial standpoint.

The present inventors conducted further research based on the above findings, and the present invention was thus accomplished.

More specifically, the present invention provides the following process for producing 2,3,3,3-tetrafluoropropene.

Item 1. A process for producing 2,3,3,3-tetrafluoropropene, comprising the steps of:

producing 2-chloro-3,3,3-trifluoropropene by reacting anhydrous hydrogen fluoride with at least one chlorine-containing compound selected from the group consisting of 1,1,1,2,3-pentachloropropane, 2,3-dichloro-1,1,1-trifluoropropane, and 1,1,2,3-tetrachloropropene in a gas phase in the presence of a fluorination catalyst while heating; and producing 2,3,3,3-tetrafluoropropene by reacting 2-chloro-3,3,3-trifluoropropene with anhydrous hydrogen fluoride in a gas phase in the presence of a fluorination catalyst while heating, the step of producing 2-chloro-3,3,3-trifluoropropene being performed after the step of producing 2,3,3,3-tetrafluoropropene.

Item 2. The process for producing 2,3,3,3-tetrafluoropropene according to Item 1, wherein the reaction temperature in the step of producing 2,3,3,3-tetrafluoropropene is higher than the reaction temperature in the step of producing 2-chloro-3,3,3-trifluoropropene.

Item 3. The process for producing 2,3,3,3-tetrafluoropropene according to Item 2, wherein the reaction temperature in the step of producing 2,3,3,3-tetrafluoropropene is 300 to 450° C., and the reaction temperature in the step of producing 2-chloro-3,3,3-trifluoropropene is 200 to 380° C.

Item 4. The process for producing 2,3,3,3-tetrafluoropropene according to Item 2 or 3, further comprising the step of reheating the products of the step of producing 2-chloro-3,3,3-trifluoropropene.

Item 5. The process for producing 2,3,3,3-tetrafluoropropene according to Item 4, wherein the step of reheating the products of the step of producing 2-chloro-3,3,3-trifluoropropene comprises elevating the temperature of a portion of the outlet side of a reactor used in the step of producing 2-chloro-3,3,3-trifluoropropene to a temperature higher than that of the other portions of the reactor.

Item 6. The process according to Item 4, wherein the step of reheating the products of the step of producing 2-chloro-3,3,3-trifluoropropene comprises heating the products using a reactor for reheating disposed downstream of the reactor used in the step of producing 2-chloro-3,3,3-trifluoropropene.

Item 7. The process according to any one of Items 1 to 6, wherein the fluorination catalyst used in the step of producing 2,3,3,3-tetrafluoropropene comprises at least one member selected from the group consisting of chromium oxides, fluorinated chromium oxides, aluminum oxides, and fluorinated aluminum oxides.

Item 8. The process according to any one of Items 1 to 7, wherein each of the fluorination catalyst used in the step of producing 2-chloro-3,3,3-trifluoropropene and the fluorination catalyst used in the step of producing 2,3,3,3-tetrafluoropropene is a chromium oxide represented by the composition formula: $CrO_m$ ($1.5<m<3$) or a fluorinated chromium oxide obtained by fluorinating the chromium oxide.

Item 9. The process according to any one of Items 1 to 8, further comprising the steps of:

separating 2,3,3,3-tetrafluoropropene from the products of the step of producing 2-chloro-3,3,3-trifluoropropene or from the products of the step of reheating the products of the step of producing 2-chloro-3,3,3-trifluoropropene; and circulating a fraction containing 2-chloro-3,3,3-trifluoropropene to the step of producing 2,3,3,3-tetrafluoropropene as a starting material.

Item 10. The process according to Item 9, wherein the separation of 2,3,3,3-tetrafluoropropene from the products of the step of producing 2-chloro-3,3,3-trifluoropropene or from the products of the step of reheating the products of the step of producing 2-chloro-3,3,3-trifluoropropene is performed by distillation.

Hereinafter, the process for producing 2,3,3,3-tetrafluoropropene of the present invention is described in detail.

(1) Features of the Process of the Present Invention

The process of the present invention comprises the step of producing 2-chloro-3,3,3-trifluoropropene, which is an intermediate product, by reacting anhydrous hydrogen fluoride with at least one chlorine-containing compound selected from the group consisting of 1,1,1,2,3-pentachloropropane (HCC-240db), 2,3-dichloro-1,1,1-trifluoropropane (HCFC-243db), and 1,1,2,3-tetrachloropropene (HCO-1230xa) in a gas phase while heating (trifluoropropene-producing reaction step); and the step of producing 2,3,3,3-tetrafluoropropene (HFO-1234yf), which is the final target product, by reacting 2-chloro-3,3,3-trifluoropropene (HCFO-1233xf) with anhydrous hydrogen fluoride in a gas phase while heating (tetrafluoropropene-producing reaction step).

The process of the present invention requires a reactor used in the tetrafluoropropene-producing reaction for producing the final target product to be disposed upstream of a reactor used in the trifluoropropene-producing reaction in the above reaction steps. The products obtained in the tetrafluoropropene-producing reaction, which contain 2,3,3,3-tetrafluoropropene, are supplied to the reactor used in the trifluoropropene-producing reaction together with the chlorine-containing compound, which is a starting material for the trifluoropropene-producing reaction. 2,3,3,3-Tetrafluoropropene passed through the reactor used in the trifluoropropene-producing reaction is separated, and 2-chloro-3,3,3-trifluoropropene obtained in this step is used as a starting material for the tetrafluoropropene-producing reaction. In particular, 2,3,3,3-tetrafluoropropene can be continuously produced by circulating 2-chloro-3,3,3-trifluoropropene obtained in the trifluoropropene-producing reaction to the reactor used in the tetrafluoropropene-producing reaction on the upstream side as a starting material.

When the tetrafluoropropene-producing reaction is performed after the trifluoropropene-producing reaction, it is necessary to supply the reaction products to the tetrafluoropropene-producing reaction step after removing a large amount of hydrogen chloride generated in the trifluoropropene-producing reaction since the large amount of hydrogen chloride adversely affect the tetrafluoropropene-producing reaction. In contrast, with the features mentioned above, the amount of hydrogen chloride generated in the tetrafluoropropene-producing reaction on the upstream side is less than the amount of hydrogen chloride generated in the trifluoropropene-producing reaction, and thus the products of the tetrafluoropropene-producing reaction can be supplied to the trifluoropropene-producing reaction without removing hydrogen chloride. Thus, equipment for separating hydrogen chloride after the tetrafluoropropene-producing reaction can be eliminated and thus equipment costs can be reduced.

Further, in the above reactions, the reaction temperature in the tetrafluoropropene-producing reaction for producing the final target product can be set to a temperature higher than that in the trifluoropropene-producing reaction for producing 2-chloro-3,3,3-trifluoropropene, which is an intermediate product. In such a case, the products of the tetrafluoropropene-producing reaction, which contain the final target product and are heated to a high temperature, are supplied to and passed through the reactor used in the trifluoropropene-producing reaction, and thus the thermal energy of the products of the tetrafluoropropene-producing reaction can be effectively used for the trifluoropropene-producing reaction. As a result, heating energy required for the trifluoropropene-producing reaction to proceed can be saved or reduced.

In this case, setting the reaction temperature in the trifluoropropene-producing reaction to a sufficiently low temperature compared to the reaction temperature in the tetrafluoropropene-producing reaction is highly advantageous in terms of energy costs. However, when the reaction temperature in the trifluoropropene-producing reaction is too low, the yield of the desired 2,3,3,3-tetrafluoropropene tends to decrease since the addition of hydrogen fluoride to 2,3,3,3-tetrafluoropropene produces a fluoropropane compound. In such a case, the yield of 2,3,3,3-tetrafluoropropene can be improved by providing a reheat region after the trifluoropropene-producing reaction step and by heating the products of the trifluoropropene-producing reaction step. In this process, simply by providing a small-scale reheat region, 2,3,3,3-tetrafluoropropene can be obtained in a high yield under conditions advantageous in terms of equipment and energy costs.

According to the process of the present invention having these features, 2,3,3,3-tetrafluoropropene can be efficiently obtained with reduced energy and equipment costs in an economically advantageous manner.

The process of the present invention is sequentially described below from the upstream step, i.e., the step of producing 2,3,3,3-tetrafluoropropene by fluorinating 2-chloro-3,3,3-trifluoropropene (tetrafluoropropene-producing reaction step).

(1) Tetrafluoropropene-Producing Reaction Step

In the tetrafluoropropene-producing reaction step in the process of the present invention, 2-chloro-3,3,3-trifluoropropene is reacted with anhydrous hydrogen fluoride in a gas phase in the presence of a fluorination catalyst while heating to obtain 2,3,3,3-tetrafluoropropene according to the following reaction formula.

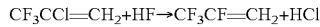

$$CF_3CCl{=}CH_2+HF\rightarrow CF_3CF{=}CH_2+HCl$$

In particular, when a fraction containing 2,3,3,3-tetrafluoropropene, which is the final target product, is separated from the products obtained in the trifluoropropene-producing reaction on the downstream side, and a fraction containing 2-chloro-3,3,3-trifluoropropene is circulated to be used as a starting material for the tetrafluoropropene-producing reaction, 2,3,3,3-tetrafluoropropene can be obtained in a continuous process. In this case, the fraction containing 2-chloro-3,3,3-trifluoropropene further contains unreacted anhydrous hydrogen fluoride among the starting materials used for the trifluoropropene-producing reaction. Thus, the unreacted anhydrous hydrogen fluoride can be also used as a starting material for the tetrafluoropropene-producing reaction.

In the tetrafluoropropene-producing reaction step, starting materials containing 2-chloro-3,3,3-trifluoropropene and anhydrous hydrogen fluoride may be, for example, heated to a predetermined temperature with a preheater and supplied to the reactor.

The fluorination reaction in the tetrafluoropropene-producing reaction step is performed in the presence of a fluorination catalyst. The usable fluorination catalysts include known catalysts that are active in a fluorination reaction with hydrogen fluoride. For example, metal oxides or fluorinated metal oxides, such as chromium oxides, fluorinated chromium oxides, aluminum oxides, and fluorinated aluminum oxides, can be used. In addition to these catalysts, metal fluorides, such as $MgF_2$, $TaF_5$, and $SbF_5$, also can be used.

Among these catalysts, although the chromium oxides, for instance, are not particularly limited, it is preferable to use a chromium oxide represented by the composition formula: $CrO_m$, wherein m falls within the range of $1.5<m<3$, more preferably $2<m<2.75$, and particularly preferably $2<m<2.3$. Chromium oxide catalysts in any form, such as powder form or pellet form, may be used, as long as they are suitable for the reaction. Of these, chromium oxide catalysts in the form of pellets are preferable. The above chromium oxide catalysts can be prepared, for example, by the process disclosed in JP5-146680A.

In addition, the fluorinated chromium oxides can be prepared by the process disclosed in JP5-146680A. For example, they can be prepared by fluorinating the chromium oxide described above with hydrogen fluoride (HF treatment).

The degree of fluorination is not particularly limited. For example, a fluorinated chromium oxide having a fluorine content of about 10 to about 45% by weight may be suitably used.

Further, a chromium-based catalyst as disclosed in JP11-171806A also may be used as a chromium oxide catalyst or fluorinated chromium oxide catalyst. The chromium-based catalyst comprises, as a main component, a chromium compound containing at least one metallic element selected from the group consisting of the metallic elements disclosed in JP11-171806A, i.e., indium, gallium, cobalt, nickel, zinc, and aluminum, and other metallic elements, i.e., vanadium, niobium, and indium. The chromium-based catalyst may be amorphous, partly crystalline, or entirely crystalline.

The fluorination catalysts described above may be used as supported on a carrier such as alumina or activated carbon.

In the tetrafluoropropene-producing reaction step, 2-chloro-3,3,3-trifluoropropene is reacted with hydrogen fluoride (HF) in a gas phase in the presence of any of the above fluorination catalysts while heating.

There is no particular limitation on the specific reaction method. When a fraction that is supplied from the products of the trifluoropropene-producing reaction step on the downstream side, which contains 2-chloro-3,3,3-trifluoropropene and anhydrous hydrogen fluoride, is circulated to the rector used in the tetrafluoropropene-producing reaction, the fraction may be further heated with a preheater together with anhydrous hydrogen fluoride that is newly supplied as required, and supplied to the reactor to be allowed to react in a gas phase. The amount of hydrogen fluoride supplied in the tetrafluoropropene-producing reaction step is generally about 1 to about 50 moles, preferably about 5 to about 30 moles, and more preferably about 7 to about 15 moles, per mole of 2-chloro-3,3,3-trifluoropropene contained in the fraction supplied from the trifluoropropene-producing reaction step.

When the amount of hydrogen fluoride contained in the fraction obtained in the trifluoropropene-producing reaction step is within the above range, a fluorination reaction in the tetrafluoropropene-producing reaction step can be performed by using only the products obtained in the trifluoropropene-producing reaction step without adding further hydrogen fluoride. When the amount of hydrogen fluoride contained in the reaction products obtained in the trifluoropropene-producing reaction step is larger than the above range, the reaction products may be used as a starting material for the tetrafluoropropene-producing reaction step after reducing the amount of hydrogen fluoride contained therein by a method such as distillation.

The selectivity of 2,3,3,3-tetrafluoropropene (HFO-1234yf) can be maintained in a desirable range by using anhydrous hydrogen fluoride within the range described above in the presence of any of the above fluorination catalysts.

The form of the reactor used in the tetrafluoropropene-producing reaction step is not particularly limited. Examples of usable reactors include an adiabatic reactor packed with a catalyst, a multitubular reactor in which a heating medium is used to cool the reactor, and the like. The reactor is preferably made of a material resistant to the corrosive action of hydrogen fluoride, such as Hastelloy, Inconel, Monel, or the like.

The reaction temperature, i.e., the temperature in the reactor, is generally about 200 to about 500° C., preferably about 300 to about 450° C., and more preferably about 350 to about 400° C. If the reaction temperature is higher than this range, the selectivity of HFO-1234yf undesirably decreases. If the reaction temperature is lower than this range, the conversion of the starting compound undesirably decreases.

The pressure during the reaction is not particularly limited, and the reaction may be performed under ordinary pressure or increased pressure. More specifically, the reaction in the present invention may be performed under atmospheric pressure (0.1 MPa), and may be also performed under an increased pressure up to about 1.0 MPa.

The reaction time is not particularly limited. However, the contact time, which is represented by W/Fo, may be generally adjusted to a range of about 5 to about 20 g·sec/cc. W/Fo is the ratio of the catalyst amount W(g) to the total flow rate Fo (flow rate at 0° C., 0.1013 MPa: cc/sec) of the starting material gases supplied (total amount of 2-chloro-3,3,3-trifluoropropene and HF).

(2) Trifluoropropene-Producing Reaction Step

In the trifluoropropene-producing reaction step, a fluorination reaction with anhydrous hydrogen fluoride is performed in a gas phase in the presence of a fluorination catalyst while heating, using at least one chlorine-containing compound selected from the group consisting of 1,1,1,2,3-pentachloropropane, 2,3-dichloro-1,1,1-trifluoropropane, and 1,1,2,3-tetrachloropropene as a starting material.

1,1,1,2,3-Pentachloropropane (HCC-240db), 2,3-dichloro-1,1,1-trifluoropropane (HCFC-243db), and 1,1,2,3-tetrachloropropene (HCO-1230xa) used as starting materials are known compounds that can be easily obtained.

The usable fluorination catalysts include known catalysts that are active in a fluorination reaction with hydrogen fluoride as in the tetrafluoropropene-producing reaction. In particular, it is preferable to use a chromium-atom-containing fluorination catalyst. By using such a catalyst and reacting the chlorine-containing compound and anhydrous hydrogen fluoride used as starting materials according to the conditions described below, 2-chloro-3,3,3-trifluoropropene (HCFC-1233xf) can be obtained with high selectivity.

Examples of usable chromium-atom-containing fluorination catalysts include halides and oxides. Of these, $CrCl_3$, $CrF_2$, $Cr_2O_3$, $CrO_2$, $CrO_2$, and the like can be given as examples of preferred catalysts. These catalysts may be supported on a carrier. There is no particular limitation on the carrier, and examples of the carrier include porous alumina silicates typified by zeolites, aluminum oxides, silicon oxides, activated carbons, titanium oxides, zirconium oxides, zinc oxides, aluminum fluorides, and the like.

In particular, in the present invention, it is preferable to use at least one catalyst selected from the group consisting of chromium oxides and fluorinated chromium oxides. As such chromium oxide catalysts or fluorinated chromium oxides, the same catalysts as used in the tetrafluoropropene-producing reaction mentioned above may be used.

Anhydrous hydrogen fluoride may be generally supplied to the reactor together with the products of the tetrafluoropropene-producing reaction step. The amount of anhydrous hydrogen fluoride used is not particularly limited. To achieve high selectivity of 2-chloro-3,3,3-trifluoropropene (HCFO-1233xf), the amount of anhydrous hydrogen fluoride used is preferably about 3 moles or more, and more preferably about 8 moles or more, per mole of the chlorine-containing compound used as a starting material. When the amount of anhydrous hydrogen fluoride is less than this range, the selectivity of HCFO-1233xf and catalytic activity tend to decrease. Thus, an amount of anhydrous hydrogen fluoride less than the above range is unfavorable.

The upper limit of the amount of anhydrous hydrogen fluoride is not particularly limited. An excessively large amount of hydrogen fluoride has little influence on selectivity and conversion. However, productivity is decreased because the amount of hydrogen fluoride to be separated increases during purification. For this reason, the amount of anhydrous hydrogen fluoride is generally preferably about 100 moles or less, and more preferably about 50 moles or less, per mole of the chlorine-containing compound used as a starting material.

A process in which a fluorination catalyst is placed into a tubular flow reactor, and the above chlorine-containing compound and anhydrous hydrogen fluoride used as starting materials are introduced to the reactor, can be given as one specific embodiment of the process of the present invention.

The reactor is preferably made of a material resistant to the corrosive action of hydrogen fluoride, such as Hastelloy, Inconel, Monel, or the like.

The lower limit of the reaction temperature is not particularly limited because the lower reaction temperature is advantageous in terms of less decomposition of the starting materials and the products. However, if the temperature is too low, a chlorine-containing compound conversion tends to decrease. For this reason, the reaction temperature is preferably 200° C. or more, and more preferably 220° C. or more.

Regarding the upper limit of the reaction temperature, an excessively high reaction temperature is not preferable because an excessively high reaction temperature notably decreases catalytic activity due to decomposition of the starting materials, and easily causes formation of $C_1$, $C_2$ compounds, and isomers, such as $CF_3CH=CHF$ and $CF_3CH=CHCl$, as by-products. For this reason, the reaction temperature is preferably about 400° C. or less. In particular, the reaction temperature in the trifluoropropene-producing reaction step is preferably about 200 to about 380° C.

In the process of the present invention, the reaction temperature in the trifluoropropene-producing reaction step is preferably within the range described above and lower than that in the tetrafluoropropene-producing reaction step. This enables effective use of reaction heat of the tetrafluoropropene-producing reaction step. Thereby, a device for heating the starting materials supplied to the reactor used in the trifluoropropene-producing reaction, which is disposed downstream of the reactor used in the tetrafluoropropene-producing reaction, can be eliminated; or, energy required for heating can be reduced.

However, when the reaction temperature in the trifluoropropene-producing reaction step is too low, the yield of 2,3,3,3-tetrafluoropropene tends to decrease since the addition reaction of hydrogen fluoride to 2,3,3,3-tetrafluoropropene, which is the final target product obtained in the tetrafluoropropene-producing reaction step, produces a fluoropropane compound. For this reason, to maintain the yield of 2,3,3,3-tetrafluoropropene within a favorable range, the reaction temperature in the trifluoropropene-producing reaction step is preferably about 300° C. or more and more preferably about 340° C. or more. To effectively use reaction heat of the tetrafluoropropene-producing reaction step and maintain the yield of 2,3,3,3-tetrafluoropropene within a favorable range, the reaction temperature in the trifluoropropene-producing reaction step is preferably lower than that in the tetrafluoropropene-producing reaction step and within the range of about 300 to about 380° C., and more preferably within the range of about 340 to about 380° C.

In addition, when the reheat region described below is used after the trifluoropropene-producing reaction step, the formation of fluoropropane compounds can be suppressed and the yield of 2,3,3,3-tetrafluoropropene can be improved. Thus, in such a case, the reaction temperature in the trifluoropropene-producing reaction step is preferably about 50 to about 150° C. lower than that in the tetrafluoropropene-producing reaction step from the viewpoint of producing 2,3,3,3-tetrafluoropropene in a high yield with reduced energy costs through effective use of reaction heat of the tetrafluoropropene-producing reaction step.

When the reaction temperature in the trifluoropropene-producing reaction step is significantly lowered relative to that in the tetrafluoropropene-producing reaction step, thermal energy obtained by heat exchange for cooling the products of tetrafluoropropene-producing reaction step may be used for heating in the reheat region. This enables significant reduction in energy costs by effectively using thermal energy of the tetrafluoropropene-producing reaction step.

The pressure during the reaction is not particularly limited, and the reaction may be performed under reduced pressure, ordinary pressure, or increased pressure. Although the reaction may be generally carried out at pressure near atmospheric pressure (0.1 MPa), it can also proceed smoothly under reduced pressure of less than 0.1 MPa. Furthermore, the reaction may be performed under increased pressure within a range in which the starting materials do not liquefy.

There is no limitation on the contact time. For example, the contact time, which is represented by W/Fo, is preferably adjusted to about 0.5 to about 50 g·sec/mL, and more preferably about 1 to about 20 g·sec/mL. W/Fo is the ratio of the catalyst amount W(g) to the total flow rate Fo (flow rate at 0° C., 0.1013 MPa: cc/sec) of the starting material gases supplied to the reaction system.

In the process of the present invention, the starting materials may be supplied to the reactor as they are, or a gas that is inert to the starting materials and catalyst, such as nitrogen, helium, or argon, may be present together with the starting materials. The concentration of the inert gas is about 0 to about 80 mol % based on the amount of the gaseous components introduced into the reactor. The inert gas may be added in either the tetrafluoropropene-producing reaction step or the trifluoropropene-producing reaction step, or in both.

Further, in the process of the present invention, one or both of oxygen and chlorine may be supplied to the reactor together with the starting materials to maintain catalytic activity for a long period of time. This enables suppression of a decrease in catalytic activity. Oxygen and chlorine may each be supplied at any reaction step.

(3) Reheating Step

In the present invention, the yield of the desired 2,3,3,3-tetrafluoropropene can be improved by reheating the products after the above trifluoropropene-producing reaction as required. As described above, when the reaction temperature is lowered in the trifluoropropene-producing reaction step, fluoropropane compounds, which are by-products of the tetrafluoroolefin-producing reaction step, are more likely to be generated. This is attributable to the equilibrium relationship between trifluoropropene and fluoropropane compounds although it depends on reaction conditions. Thus, by heating the products of the trifluoropropene-producing reaction step to shift the equilibrium toward formation of 2,3,3,3-tetrafluoropropene, the amount of 2,3,3,3-tetrafluoropropene produced can be increased.

Reheating is performed after the trifluoropropene-producing reaction step and before the separation of 2,3,3,3-tetrafluoropropene from the products.

The reheating temperature is not particularly limited. The amount of 2,3,3,3-tetrafluoropropene produced increases as the reheating temperature rises. Thus, the yield of 2,3,3,3-tetrafluoropropene can be increased by setting the reheating temperature to a temperature higher than that in the trifluoropropene-producing reaction step. In particular, when the reheating temperature is equal to or higher than the reaction temperature in the tetrafluoropropene-producing reaction step, 2,3,3,3-tetrafluoropropene can be obtained in an amount equal to or larger than the amount of 2,3,3,3-tetrafluoropropene produced in the tetrafluoropropene-producing reaction step. The upper limit of the reheating temperature is not particularly limited, but is generally about 500° C. or less, and preferably about 450° C. or less. The specific reheating temperature may be determined considering energy costs, yield, or the like.

As an example of a specific reheating method, a portion of the outlet side of the reactor used in the trifluoropropene-producing reaction step may be used as a reheat region, or a reactor for reheating may be disposed downstream of the reactor used in the trifluoropropene-producing reaction step.

When a reactor for reheating is disposed, it is preferably made of a material resistant to the corrosive action of hydrogen fluoride, such as Hastelloy, Inconel, Monel, or the like.

In reheating, a catalyst may be used as required. Use of a catalyst enables the yield of 2,3,3,3-tetrafluoropropene to be increased with a smaller reheating device. Examples of usable catalysts include the catalyst used in the tetrafluoropropene-producing reaction step, the catalyst used in the trifluoropropene-producing reaction step, and the like.

The pressure during reheating is not particularly limited. The reheating may be performed under ordinary pressure or increased pressure; however, to maintain the equilibrium toward tetrafluoropropene, a lower pressure is suitable, and a pressure at around atmospheric pressure is preferable. When a portion of the outlet side of the reactor used in the trifluoropropene-producing reaction step is used for reheating, the pressure during the reheating may be the same as that of the trifluoropropene-producing reaction.

The reheating time varies depending on the heating temperature, pressure, type of a catalyst used and thus cannot be completely specified; however, even if the reheating time is short, the content of 2,3,3,3-tetrafluoropropene in the products can be increased since shift in an equilibrium due to the elimination of hydrogen fluoride from fluoropropane compounds proceeds in a relatively short time. For example, when a portion of the outlet side of the reactor used in the trifluoropropene-producing reaction step is used as a reheat region, a portion of the reactor having a volume that is about ¼ to about 1/10 of the total volume of the reactor may be used as a reheat region. When a reactor for reheating is disposed downstream of the reactor used in the trifluoropropene-producing reaction step, it is sufficient that the volume of the reactor for reheating is about ⅓ to about ⅛ of the volume of the reactor used in the trifluoropropene-producing reaction step. Thus, the costs required for equipment can be minimized even when the reheating step is added.

As an example of the reaction time when a catalyst is used, the contact time, which is represented by W/Fo, is adjusted to the range of about 0.5 to about 5 g·sec/cc. W/Fo is the ratio of the catalyst amount W(g) to the total flow rate Fo (flow rate at 0° C., 0.1013 Ma: cc/sec) of the starting material gases supplied.

(4) Reaction Products

After the trifluoropropene-producing reaction is performed in the above manner, and the products of the trifluoropropene-producing reaction are reheated as required, 2,3,3,3-tetrafluoropropene is separated from the resulting products, thereby obtaining the desired 2,3,3,3-tetrafluoropropene. As a method for separating 2,3,3,3-tetrafluoropropene, any means, such as distillation, liquid separation, extraction, or extractive distillation, may be used.

For example, when distillation operation is performed as a separation means, 2,3,3,3-tetrafluoropropene, which is a product of the tetrafluoropropene-producing reaction, can be separated as a column top fraction among components contained in the products of the trifluoropropene-producing reaction. The column top fraction contains hydrogen chloride and the like in addition to 2,3,3,3-tetrafluoropropene. Thus, by separating hydrogen chloride with a separation device, 2,3,3,3-tetrafluoropropene, which is the final target product, can be obtained. For separating hydrogen chloride, a method such as water washing may be used.

2-Chloro-3,3,3-trifluoropropene (HCFO-1233xf) and unreacted hydrogen fluoride that are obtained by distillation as a column bottom fraction can be used as starting materials for the tetrafluoropropene-producing reaction. Thus, by heating the column bottom fraction with a preheater and circulating it to the reactor used in the tetrafluoropropene-producing reaction step, 2,3,3,3-tetrafluoropropene can be efficiently obtained in a continuous process.

Advantageous Effects of Invention

According to the process of the present invention, 2,3,3,3-tetrafluoropropene can be efficiently produced with reduced energy and equipment costs in an economically advantageous manner, using at least one chlorine-containing compound selected from the group consisting of 1,1,1,2,3-pentachloropropane, 2,3-dichloro-1,1,1-trifluoropropane, and 1,1,2,3-tetrachloropropene as a starting material.

DESCRIPTION OF EMBODIMENTS

Hereinafter, the present invention will be described in more detail with reference to the Examples below.

Example 1

Figure 1:
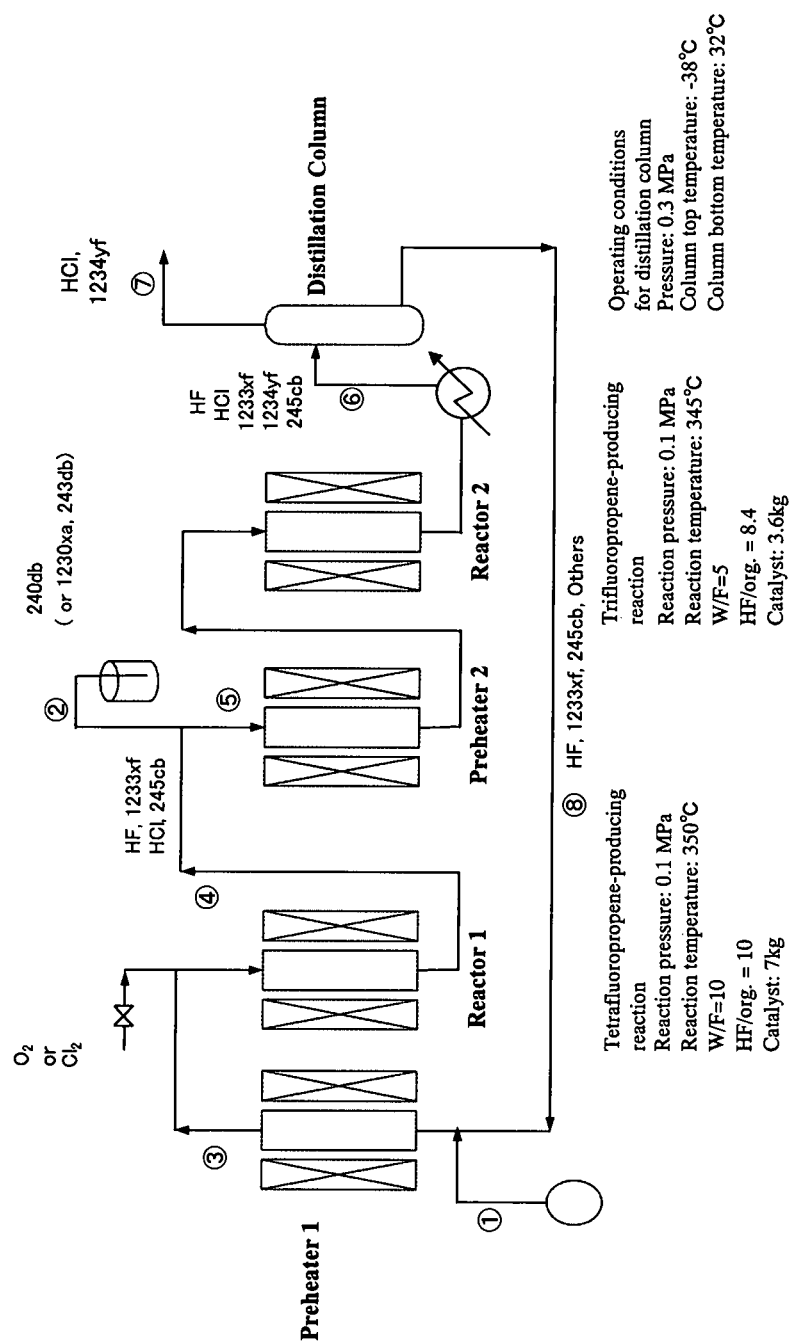
FIG. 1 is a flowchart of the reaction process in Examples 1 to 3.

2,3,3,3-tetrafluoropropene was produced by using 1,1,1,2,3-pentachloropropane (HCC-240db) as a starting material, following the flow chart shown in FIG. 1.

A Hastelloy reactor with a capacity of 6 L was used as a reactor for the tetrafluoropropene-producing reaction step (reactor 1), and 7 kg of chromium oxide primarily containing $CrO_2$ was packed into the reactor as a catalyst. A Hastelloy reactor with a capacity of 3.4 L was used as a reactor for the trifluoropropene-producing reaction step (reactor 2), and 3.6 kg of chromium oxide primarily containing $CrO_2$ was packed into the reactor as a catalyst.

Anhydrous hydrogen fluoride diluted with nitrogen was passed through these reactors, and the temperature of the reactors was raised stepwise from 200° C. to 360° C. Fluorination at 360° C. for 220 hours gave a fluorinated chromium oxide catalyst containing about 31 wt % of fluorine in both reactors. The fluorinated catalyst was used for reaction without being removed.

While allowing nitrogen to flow into the reactors, the reactors and preheaters were each heated with an electric furnace. After a predetermined temperature was reached, 2-chloro-3,3,3-trifluoropropene (HCFO-1233xf) and anhydrous hydrogen fluoride, which had been fed into a distillation column in advance, were supplied into a preheater 1 by using a pump and, after being heated with the preheater 1, were introduced into the reactor for the tetrafluoropropene-producing reaction step (reactor 1) to start a circulation operation of the system shown in FIG. 1. After the conversion and selectivity in the tetrafluoropropene-producing reaction step became stabilized, 1,1,1,2,3-pentachloropropane (HCC-240db) to be used as a starting material was heated with a preheater 2, and supplied into the reactor for the trifluoropropene-producing reaction step (reactor 2) to start an operation of the process shown in FIG. 1.

The operating conditions of the reactor for the tetrafluoropropene-producing reaction step (reactor 1) were as follows: a pressure of 0.1 MPa, a temperature of 350° C., a contact time ($W/F_0$) of 10, and a molar ratio of HF to 2-chloro-3,3,3-trifluoropropene of 10. The operating conditions of the reactor for the trifluoropropene-producing reaction step (reactor 2) were as follows: a pressure of 0.1 MPa, a temperature of 345° C., a contact time ($W/F_0$) of 5, and a molar ratio of HF to the total amount of 245cb, 1233xf, and 240db of 8.4. The operating conditions of the distillation column were as follows: a pressure of 0.3 MPa, a column top temperature of −38° C., and a column bottom temperature of 32° C.

50 hours after the operation of the process started, the composition of components in each stage of the reaction process was analyzed using gas chromatography. Table 1 below shows the results. The numbers shown in the top row of Table 1 correspond to Flow numbers of the reaction process shown in FIG. 1.

The structure of each product thus produced is as follows:

$CF_3CF=CH_2$ (HFO-1234yf);

$CF_3CF_2CH_3$ (HFC-245cb);

$CF_3CH=CH_2$ (HFO-1243zf);

$CF_3CCl=CH_2$ (HCFO-1233xf); and $CCl_3CHClCH_2Cl$ (HCC-240db).

TABLE 1

| | Flow | | | | | | | |
|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr |
| HF | 5.82 | 0.00 | 102 | 100.8 | 100.8 | 97.1 | 0.46 | 96.6 |
| HCl | 0.00 | 0.00 | 0.00 | 1.22 | 1.22 | 6.10 | 6.10 | 0.00 |
| 1234yf | 0.00 | 0.00 | 0.01 | 1.22 | 1.22 | 1.22 | 1.20 | 0.01 |
| 245cb | 0.00 | 0.00 | 0.41 | 0.41 | 0.41 | 0.41 | 0.00 | 0.41 |
| 1233xf | 0.00 | 0.00 | 10.2 | 9.03 | 9.0 | 10.2 | 0.00 | 10.2 |
| 240db | 0.00 | 1.27 | 0.01 | 0.00 | 1.27 | 0.01 | 0.00 | 0.01 |
| O2 | 0.00 | 0.00 | 1.02 | 1.02 | 1.02 | 1.02 | 1.02 | 0.00 |
| Others | 0.00 | 0.00 | 0.14 | 0.11 | 0.11 | 0.14 | 0.00 | 0.14 |

As is apparent from the results above, according to the process of Example 1, the desired product, i.e., 2,3,3,3-tetrafluoropropene (HFO-1234yf), was obtained in a continuous and stable manner without having to install a distillation apparatus and a hydrochloric acid separator after the tetrafluoropropene-producing step.

Example 2

A gas-phase two-stage fluorination reaction using HF was carried out by following the procedure of Example 1 and using 1,1,2,3-tetrachloropropene (HCO-1230xa) in place of 1,1,1,2,3-pentachloropropane (HCC-240db) as a starting material, thereby giving 2,3,3,3-tetrafluoropropene (HFO-1234yf).

Table 2 below shows the results of analyzing components in each stage of the reaction process.

TABLE 2

| | Flow | | | | | | | |
|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr |
| HF | 5.80 | 0.00 | 102 | 100.8 | 100.8 | 97.1 | 0.46 | 96.6 |
| HCl | 0.00 | 0.00 | 0.00 | 1.22 | 1.22 | 4.88 | 4.88 | 0.00 |
| 1234yf | 0.00 | 0.00 | 0.02 | 1.22 | 1.22 | 1.22 | 1.20 | 0.02 |
| 245cb | 0.00 | 0.00 | 0.41 | 0.41 | 0.41 | 0.41 | 0.00 | 0.41 |
| 1233xf | 0.00 | 0.00 | 10.2 | 9.03 | 9.03 | 10.2 | 0.00 | 10.2 |
| 1230xa | 0.00 | 1.27 | 0.01 | 0.00 | 1.27 | 0.01 | 0.00 | 0.01 |
| O2 | 0.00 | 0.00 | 1.02 | 1.02 | 1.02 | 1.02 | 1.02 | 0.00 |
| Others | 0.00 | 0.00 | 0.14 | 0.11 | 0.11 | 0.14 | 0.00 | 0.14 |

As is apparent from Table 2, when 1,1,2,3-tetrachloropropene (HCO-1230xa) was used as a starting material, the desired product, i.e., 2,3,3,3-tetrafluoropropene (HFO-1234yf), was also obtained in a continuous and stable manner by carrying out the process shown in FIG. 1.

Example 3

A gas-phase two-stage fluorination reaction using HF was carried out by following the procedure of Example 1 and using 2,3-dichloro-1,1,1-trifluoropropane (HCFC-243db) in place of 1,1,1,2,3-pentachloropropane (HCC-240db) as a starting material, thereby giving 2,3,3,3-tetrafluoropropene (HFO-1234yf). Table 3 below shows the results of analyzing components in each stage of the reaction process.

TABLE 3

| | Flow | | | | | | | |
|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr |
| HF | 2.11 | 0.00 | 102 | 100.8 | 100.8 | 100.8 | 0.48 | 100.3 |
| HCl | 0.00 | 0.00 | 0.00 | 1.22 | 1.22 | 2.44 | 2.44 | 0.00 |
| 1234yf | 0.00 | 0.00 | 0.01 | 1.22 | 1.22 | 1.22 | 1.20 | 0.01 |
| 245cb | 0.00 | 0.00 | 0.41 | 0.41 | 0.41 | 0.41 | 0.00 | 0.41 |
| 1233xf | 0.00 | 0.00 | 10.2 | 8.99 | 8.99 | 10.2 | 0.00 | 1.02 |
| 243db | 0.00 | 1.25 | 0.01 | 0.00 | 1.25 | 0.01 | 0.00 | 0.01 |
| O2 | 0.00 | 0.00 | 1.02 | 1.02 | 1.02 | 1.02 | 1.02 | 0.00 |
| Others | 0.00 | 0.00 | 0.10 | 0.10 | 0.10 | 0.10 | 0.00 | 0.10 |

As is apparent from Table 3, when 2,3-dichloro-1,1,1-trifluoropropane (HCFC-243db) was used as a starting material, the desired product, i.e., 2,3,3,3-tetrafluoropropene (HFO-1234yf), was also obtained in a continuous and stable manner by carrying out the process shown in FIG. 1, as was the case when 1,1,1,2,3-pentachloropropane (HCC-240db) was used as a starting material.

Example 4

Figure 2:
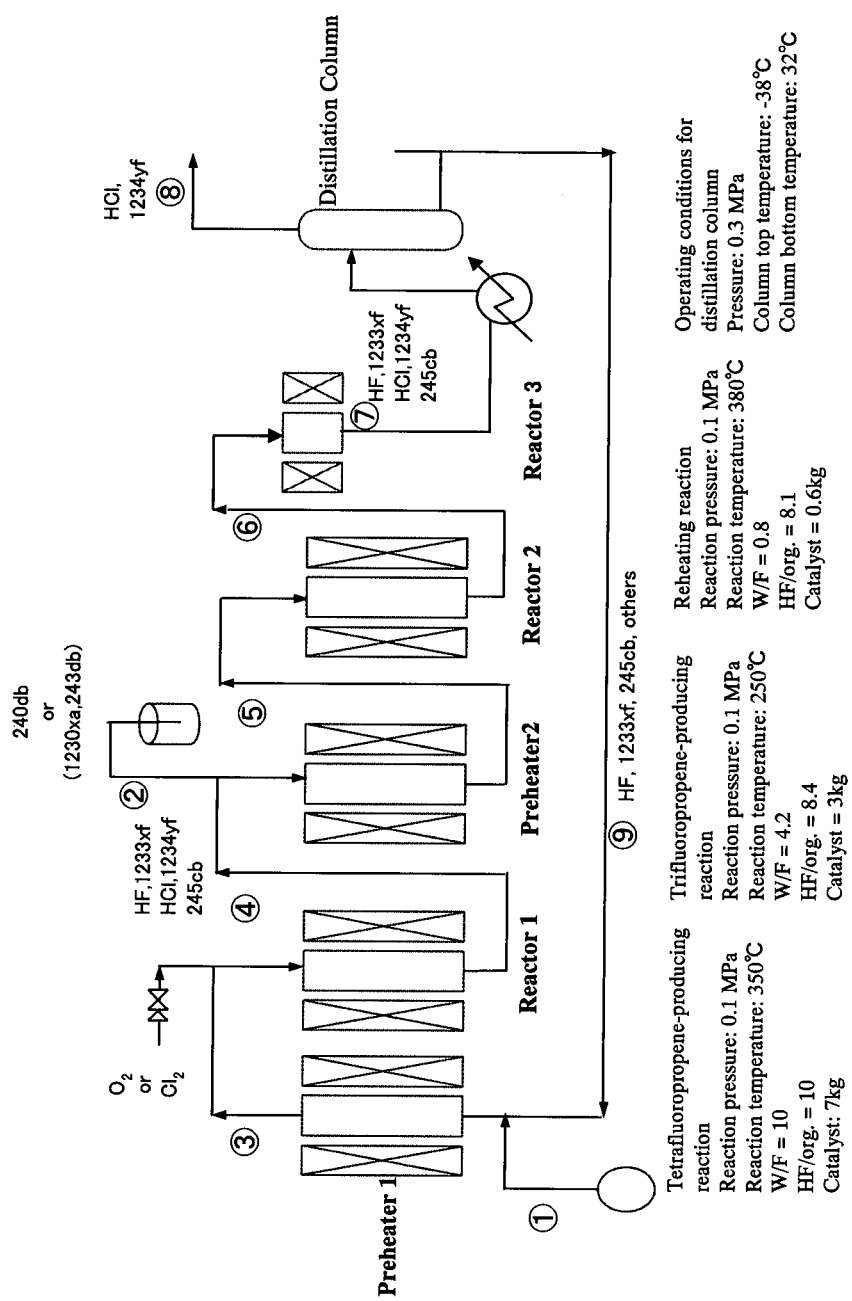
FIG. 2 is a flowchart of the reaction process in Examples 4, 6, and 8.

2,3,3,3-tetrafluoropropene was produced by using 1,1,1,2,3-pentachloropropane (HCC-240db) as a starting material, following the flow chart shown in FIG. 2.

A Hastelloy reactor with a capacity of 6 L was used as a reactor for the tetrafluoropropene-producing reaction step (reactor 1), and 7 kg of chromium oxide primarily containing $CrO_2$ was packed into the reactor as a catalyst. A Hastelloy reactor with a capacity of 3 L was used as a reactor for the trifluoropropene-producing reaction step (reactor 2), and 3 kg of chromium oxide primarily containing $CrO_2$ was packed into the reactor as a catalyst. A Hastelloy reactor with a capacity of 0.5 L was used as a reheater (reactor 3), and 0.6 kg of chromium oxide primarily containing $CrO_2$ was packed into the reactor as a catalyst.

The operating procedure from the fluorination treatment of the catalyst to the start of the reaction was carried out in the same manner as in Example 1.

The operating conditions of the reactor for the tetrafluoropropene-producing reaction step (reactor 1) were as follows: a pressure of 0.1 MPa, a temperature of 350° C., a contact time ($W/F_0$) of 10, and a molar ratio of HF to 2-chloro-3,3,3-trifluoropropene of 10. The operating conditions of the reactor for the trifluoropropene-producing reaction step (reactor 2) were as follows: a pressure of 0.1 MPa, a temperature of 250° C., a contact time ($W/F_0$) of 4.2, and a molar ratio of HF to the total amount of 245cb, 1233xf, and 240db of 8.4. The operating conditions of the reheater (reactor 3) were as follows: a pressure of 0.1 MPa, a temperature of 380° C., and a contact time (W/Fo) of 0.8. The operating conditions of the distillation column were as follows: a pressure of 0.3 MPa, a column top temperature of −38° C., and a column bottom temperature of 32° C.

50 hours after the operation of the process started, the composition of components in each stage of the reaction process was analyzed using gas chromatography. Table 4 below shows the results. The numbers shown in the top row of Table 4 correspond to Flow numbers of the reaction process shown in FIG. 2.

TABLE 4

| | Flow | | | | | | | | |
|---|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr | ⑨ mol/hr |
| HF | 5.82 | 0.00 | 102 | 100.8 | 100.8 | 96.0 | 97.1 | 0.46 | 96.6 |
| HCl | 0.00 | 0.00 | 0.00 | 1.22 | 1.22 | 6.10 | 6.10 | 6.10 | 0.00 |
| 1234yf | 0.00 | 0.00 | 0.01 | 1.22 | 1.22 | 0.15 | 1.22 | 1.20 | 0.01 |
| 245cb | 0.00 | 0.00 | 0.41 | 0.41 | 0.41 | 1.48 | 0.41 | 0.00 | 0.41 |
| 1233xf | 0.00 | 0.00 | 10.2 | 9.03 | 9.0 | 10.2 | 10.2 | 0.00 | 10.2 |
| 240db | 0.00 | 1.27 | 0.01 | 0.00 | 1.27 | 0.01 | 0.01 | 0.00 | 0.01 |
| O2 | 0.00 | 0.0 | 1.02 | 1.02 | 1.02 | 1.02 | 1.02 | 1.02 | 0.00 |
| Others | 0.00 | 0.00 | 0.14 | 0.11 | 0.11 | 0.11 | 0.14 | 0.00 | 0.14 |

As is apparent from the results above, in the process shown in FIG. 2, heating energy required in the trifluoropropene-producing reaction step was substantially reduced because the temperature of the reactor for the trifluoropropene-producing reaction step (reactor 2) was set significantly lower than the temperature of the reactor for the tetrafluoropropene-producing reaction step (reactor 1). Moreover, the content of 2,3,3,3-tetrafluoropropene in the efflux gas (flow 7) from the reheater (reactor 3) was equivalent to the content of 2,3,3,3-tetrafluoropropene in the efflux gas (flow 4) from the reactor for the tetrafluoropropene-producing reaction step (reactor 1). Thus, the amount of 2,3,3,3-tetrafluoropropene generated by the tetrafluoropropene-producing reaction was maintained by installing a small-scale reheater (reactor 3) used after the trifluoropropene-producing reaction step.

It was confirmed from the results that according to the process shown in FIG. 2, the desired product, i.e., 2,3,3,3-tetrafluoropropene (HFO-1234yf), can be obtained in a continuous and stable manner with an excellent yield while effectively using the reaction heat of the tetrafluoropropene-producing reaction step.

The operating procedure from the fluorination treatment of the catalyst to the start of the reaction was carried out in the same manner as in Example 1. The operating conditions for the distillation column were as follows: a pressure of 0.3 MPa, a column top temperature of −38° C., and a column bottom temperature of 32° C.

50 hours after the operation of the process started, the composition of components in each stage of the reaction process was analyzed using gas chromatography. Table 5 below shows the results. The numbers shown in the top row of Table 5 correspond to Flow numbers of the reaction process shown in FIG. 3.

TABLE 5

|  | Flow | | | | | | | |
| --- | --- | --- | --- | --- | --- | --- | --- | --- |
|  | ① mol/hr | ② mol/hr | ③ mol/hr | ④ mol/hr | ⑤ mol/hr | ⑥ mol/hr | ⑦ mol/hr | ⑧ mol/hr |
| HF | 5.82 | 0.00 | 102 | 100.8 | 100.8 | 97.1 | 0.46 | 96.6 |
| HCl | 0.00 | 0.00 | 0.00 | 1.22 | 1.22 | 6.10 | 6.10 | 0.00 |
| 1234yf | 0.00 | 0.00 | 0.01 | 1.22 | 1.22 | 1.22 | 1.20 | 0.01 |
| 245cb | 0.00 | 0.00 | 0.41 | 0.41 | 0.41 | 0.41 | 0.00 | 0.41 |
| 1233xf | 0.00 | 0.00 | 10.2 | 9.03 | 9.0 | 10.2 | 0.00 | 10.2 |
| 240db | 0.00 | 1.27 | 0.01 | 0.00 | 1.27 | 0.01 | 0.00 | 0.01 |
| O2 | 0.00 | 0.0 | 1.02 | 1.02 | 1.02 | 1.02 | 1.02 | 0.00 |
| Others | 0.00 | 0.00 | 0.14 | 0.11 | 0.11 | 0.14 | 0.00 | 0.14 |

Example 5

Figure 3:
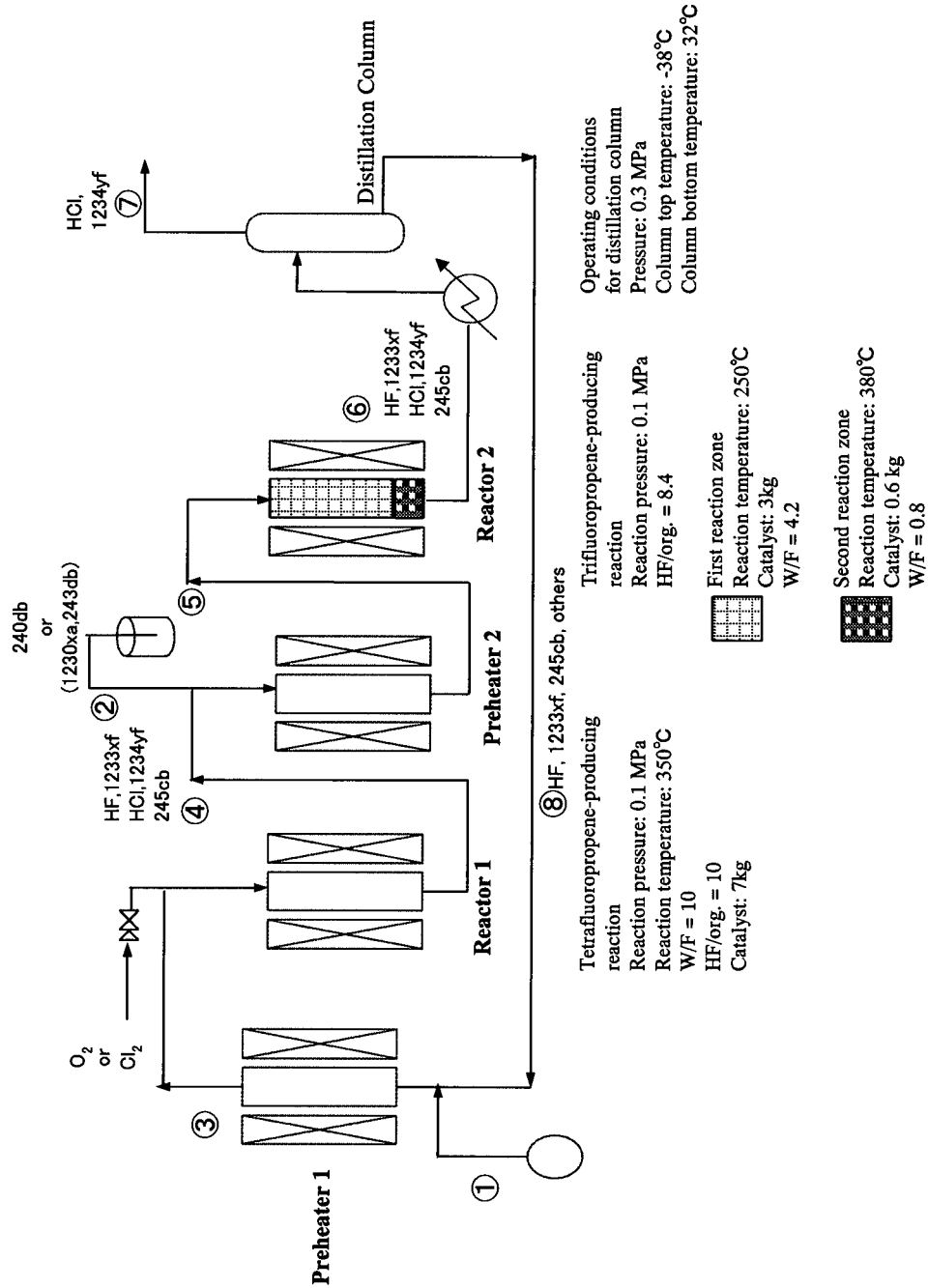
FIG. 3 is a flowchart of the reaction process in Examples 5, 7, and 9.

2,3,3,3-tetrafluoropropene was produced by using 1,1,1,2,3-pentachloropropane (HCC-240db) as a starting material, following the flow chart shown in FIG. 3.

A Hastelloy reactor with a capacity of 6 L was used as a reactor for the tetrafluoropropene-producing reaction step (reactor 1), and 7 kg of chromium oxide primarily containing $CrO_2$ was packed into the reactor as a catalyst. The operating conditions were as follows: a pressure of 0.1 MPa, a temperature of 350° C., a contact time ($W/F_0$) of 10, and a molar ratio of HF to 2-chloro-3,3,3-trifluoropropene of 10.

A Hastelloy reactor with a capacity of 3 L was used as a reactor for the trifluoropropene-producing reaction step (reactor 2), and 3.6 kg of chromium oxide primarily containing $CrO_2$ was packed into the reactor as a catalyst. The operating conditions were as follows: a pressure of 0.1 MPa, and a molar ratio of HF to the total amount of 245cb, 1233xf, and 240db of 8.4. The temperature of the region located adjacent to the reactor inlet and containing 3 kg of the catalyst was set at 250° C., and the temperature of the region located adjacent to the reactor outlet and containing 0.6 kg of the catalyst was set at 380° C. The latter was provided to serve as a reheating region for resulting products from the trifluoropropene-producing reaction step.

Also in the process shown in FIG. 3, heating energy required in the trifluoropropene-producing reaction step was substantially reduced because the temperature of the reactor for the trifluoropropene-producing reaction step (reactor 2) was set significantly lower than the temperature of the reactor for the tetrafluoropropene-producing reaction step (reactor 1). Moreover, by setting high the temperature of the region at the outlet side of reactor 2 so as to serve as a reheating region, the content of 2,3,3,3-tetrafluoropropene in the efflux gas (flow 6) became equivalent to the content of 2,3,3,3-tetrafluoropropene in the efflux gas (flow 4) from the reactor for the tetrafluoropropene-producing reaction step (reactor 1). Thus, it was confirmed from the results that the amount of 2,3,3,3-tetrafluoropropene generated by the tetrafluoropropene-producing reaction can also be maintained by using a process in which the temperature of the region at the outlet side of the reactor for the trifluoropropene-producing reaction step is set high.

Example 6

A gas-phase fluorination reaction using HF was carried out by following the procedure of Example 4 and using 1,1,2,3-tetrachloropropene (HCO-1230xa) in place of 1,1,1,2,3-pentachloropropane (HCC-240db) as a starting material, thereby giving 2,3,3,3-tetrafluoropropene (HFO-1234yf). Table 6 below shows the results of analyzing components in each stage of the reaction process.

TABLE 6

| | Flow | | | | | | | | |
|---|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr | ⑨ mol/hr |
| HF | 5.80 | 0.00 | 102 | 100.8 | 100.8 | 96.0 | 97.1 | 0.46 | 96.6 |
| HCl | 0.00 | 0.00 | 0.00 | 1.22 | 1.22 | 4.88 | 4.88 | 4.88 | 0.00 |
| 1234yf | 0.00 | 0.00 | 0.02 | 1.22 | 1.22 | 0.15 | 1.22 | 1.20 | 0.02 |
| 245cb | 0.00 | 0.00 | 0.41 | 0.41 | 0.41 | 1.48 | 0.41 | 0.00 | 0.41 |
| 1233xf | 0.00 | 0.00 | 10.2 | 9.03 | 9.03 | 10.2 | 10.2 | 0.00 | 10.2 |
| 1230xa | 0.00 | 1.27 | 0.01 | 0.00 | 1.27 | 0.01 | 0.01 | 0.00 | 0.01 |
| O2 | 0.00 | 0.0 | 1.02 | 1.02 | 1.02 | 1.02 | 1.02 | 1.02 | 0.00 |
| Others | 0.00 | 0.00 | 0.14 | 0.11 | 0.11 | 0.11 | 0.14 | 0.00 | 0.14 |

As is apparent from Table 6, it was confirmed that when 1,1,2,3-tetrachloropropene (HCO-1230xa) was used as a starting material, the process shown in FIG. 2 also enables maintaining the amount of 1234yf generated by the tetrafluoropropene-producing reaction with less heating energy consumed.

Example 7

A gas-phase fluorination reaction using HF was carried out by following the procedure of Example 5 and using 1,1,2,3-tetrachloropropene (HCO-1230xa) in place of 1,1,1,2,3-pentachloropropane (HCC-240db) as a starting material, thereby giving 2,3,3,3-tetrafluoropropene (HFO-1234yf). Table 7 below shows the results of analyzing components in each stage of the reaction process.

TABLE 7

| | Flow | | | | | | | |
|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr |
| HF | 5.80 | 0.00 | 102 | 100.8 | 100.8 | 97.1 | 0.46 | 96.6 |
| HCl | 0.00 | 0.00 | 0.00 | 1.22 | 1.22 | 4.88 | 4.88 | 0.00 |
| 1234yf | 0.00 | 0.00 | 0.02 | 1.22 | 1.22 | 1.22 | 1.20 | 0.02 |
| 245cb | 0.00 | 0.00 | 0.41 | 0.41 | 0.41 | 0.41 | 0.00 | 0.41 |
| 1233xf | 0.00 | 0.00 | 10.2 | 9.03 | 9.03 | 10.2 | 0.00 | 10.2 |
| 1230xa | 0.00 | 1.27 | 0.01 | 0.00 | 1.27 | 0.01 | 0.00 | 0.01 |
| O2 | 0.00 | 0.0 | 1.02 | 1.02 | 1.02 | 1.02 | 1.02 | 0.00 |
| Others | 0.00 | 0.00 | 0.14 | 0.11 | 0.11 | 0.14 | 0.00 | 0.14 |

As is apparent from Table 7, it was confirmed that when 1,1,2,3-tetrachloropropene (HCO-1230xa) was used as a starting material, the process shown in FIG. 3 also enables maintaining the amount of 1234yf generated by the tetrafluoropropene-producing reaction with less heating energy consumed.

Example 8

A gas-phase fluorination reaction using HF was carried out by following the procedure of Example 4 and using 2,3-dichloro-1,1,1-trifluoropropane (HCFC-243db) in place of 1,1,1,2,3-pentachloropropane (HCC-240db) as a starting material, thereby giving 2,3,3,3-tetrafluoropropene (HFO-1234yf). Table 8 below shows the results of analyzing components in each stage of the reaction process.

TABLE 8

| | Flow | | | | | | | | |
|---|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr | ⑨ mol/hr |
| HF | 2.11 | 0.00 | 102 | 100.8 | 100.8 | 99.7 | 100.8 | 0.48 | 100.3 |
| HCl | 0.00 | 0.00 | 0.00 | 1.22 | 1.22 | 2.44 | 2.44 | 2.44 | 0.00 |
| 1234yf | 0.00 | 0.00 | 0.01 | 1.22 | 1.22 | 0.15 | 1.22 | 1.20 | 0.01 |
| 245cb | 0.00 | 0.00 | 0.41 | 0.41 | 0.41 | 1.48 | 0.41 | 0.00 | 0.41 |
| 1233xf | 0.00 | 0.00 | 10.2 | 8.99 | 8.99 | 8.99 | 10.2 | 0.00 | 10.2 |
| 243db | 0.00 | 1.25 | 0.01 | 0.00 | 1.25 | 0.01 | 0.01 | 0.00 | 0.01 |
| O2 | 0.00 | 0.0 | 1.02 | 1.02 | 1.02 | 1.02 | 1.02 | 1.02 | 0.00 |
| Others | 0.00 | 0.00 | 0.10 | 0.10 | 0.10 | 0.10 | 0.10 | 0.00 | 0.10 |

As is apparent from Table 8, it was confirmed that when 2,3-dichloro-1,1,1-trifluoropropane (HCFC-243db) was used as a starting material, the process shown in FIG. 2 also enables maintaining the amount of 1234yf generated by the tetrafluoropropene-producing reaction with less heating energy consumed.

Example 9

A gas-phase fluorination reaction using HF was carried out by following the procedure of Example 5 and using 2,3-dichloro-1,1,1-trifluoropropane (HCFC-243db) in place of 1,1,1,2,3-pentachloropropane (HCC-240db) as a starting material, thereby giving 2,3,3,3-tetrafluoropropene (HFO-1234yf). Table 9 below shows the results of analyzing components in each stage of the reaction process.

TABLE 9

| | Flow | | | | | | | |
|---|---|---|---|---|---|---|---|---|
| | ① mol/hr | ② mol/hr | ③ mol/hr | ④ mol/hr | ⑤ mol/hr | ⑥ mol/hr | ⑦ mol/hr | ⑧ mol/hr |
| HF | 2.11 | 0.00 | 102 | 100.8 | 100.8 | 100.8 | 0.48 | 100.3 |
| HCl | 0.00 | 0.00 | 0.00 | 1.22 | 1.22 | 2.44 | 2.44 | 0.00 |
| 1234yf | 0.00 | 0.00 | 0.01 | 1.22 | 1.22 | 1.22 | 1.20 | 0.01 |
| 245cb | 0.00 | 0.00 | 0.41 | 0.41 | 0.41 | 0.41 | 0.00 | 0.41 |
| 1233xf | 0.00 | 0.00 | 10.2 | 8.99 | 8.99 | 10.2 | 0.00 | 10.2 |
| 243db | 0.00 | 1.25 | 0.01 | 0.00 | 1.25 | 0.01 | 0.00 | 0.01 |
| O2 | 0.00 | 0.0 | 1.02 | 1.02 | 1.02 | 1.02 | 1.02 | 0.00 |
| Others | 0.00 | 0.00 | 0.10 | 0.10 | 0.10 | 0.10 | 0.00 | 0.10 |

As is apparent from Table 9, it was confirmed that when 2,3-dichloro-1,1,1-trifluoropropane (HCFC-243db) was used as a starting material, the process shown in FIG. 3 also enables maintaining the amount of 1234yf generated by the tetrafluoropropene-producing reaction with less heating energy consumed.

The invention claimed is:

1. A process for producing 2,3,3,3-tetrafluoropropene, comprising the steps of:
   producing 2-chloro-3,3,3-trifluoropropene by reacting anhydrous hydrogen fluoride with at least one chlorine-containing compound selected from the group consisting of 1,1,1,2,3-pentachloropropane, 2,3-dichloro-1,1,1-trifluoropropane, and 1,1,2,3-tetrachloropropene in a gas phase in the presence of a fluorination catalyst while heating to produce products comprising 2-chloro-3,3,3-trifluoropropene; and
   producing 2,3,3,3-tetrafluoropropene by reacting 2-chloro-3,3,3-trifluoropropene with anhydrous hydrogen fluoride in a gas phase in the presence of a fluorination catalyst while heating to produce products comprising 2,3,3,3-tetrafluoropropene,
   the step of producing 2,3,3,3-tetrafluoropropene is performed upstream of the step of producing 2-chloro-3,3,3-trifluoropropene, and
   wherein 2,3,3,3-tetrafluoropropene can be continuously produced by circulating 2-chloro-3,3,3-trifluoropropene obtained in the trifluoropropene-producing step to the step of producing 2,3,3,3-tetrafluoropropene.

2. The process for producing 2,3,3,3-tetrafluoropropene according to claim 1, wherein the reaction temperature in the step of producing 2,3,3,3-tetrafluoropropene is higher than the reaction temperature in the step of producing 2-chloro-3,3,3-trifluoropropene.

3. The process for producing 2,3,3,3-tetrafluoropropene according to claim 2, wherein the reaction temperature in the step of producing 2,3,3,3-tetrafluoropropene is 300 to 450° C., and the reaction temperature in the step of producing 2-chloro-3,3,3-trifluoropropene is 200 to 380° C.

4. The process for producing 2,3,3,3-tetrafluoropropene according to claim 2, further comprising the step of reheating the products of the step of producing 2-chloro-3,3,3-trifluoropropene.

5. The process for producing 2,3,3,3-tetrafluoropropene according to claim 4, wherein the step of reheating the products of the step of producing 2-chloro-3,3,3-trifluoropropene comprises elevating the temperature of a portion of the outlet side of a reactor used in the step of producing 2-chloro-3,3,3-trifluoropropene to a temperature higher than that of the other portions of the reactor.

6. The process according to claim 4, wherein the step of reheating the products of the step of producing 2-chloro-3,3,3-trifluoropropene comprises heating the products using a reactor for reheating disposed downstream of the reactor used in the step of producing 2-chloro-3,3,3-trifluoropropene.

7. The process according to claim 1, wherein the fluorination catalyst used in the step of producing 2,3,3,3-tetrafluoropropene comprises at least one member selected from the group consisting of chromium oxides, fluorinated chromium oxides, aluminum oxides, and fluorinated aluminum oxides.

8. The process according to claim 1, wherein each of the fluorination catalyst used in the step of producing 2-chloro-3,3,3-trifluoropropene and the fluorination catalyst used in the step of producing 2,3,3,3-tetrafluoropropene is a chromium oxide represented by the composition formula: $CrO_m$ ($1.5<m<3$) or a fluorinated chromium oxide obtained by fluorinating the chromium oxide.

9. The process according to claim 4, further comprising the steps of:
   separating 2,3,3,3-tetrafluoropropene from the products of the step of producing 2-chloro-3,3,3-trifluoropropene or from the products of the step of reheating the products of the step of producing 2-chloro-3,3,3-trifluoropropene; and
   circulating a fraction containing 2-chloro-3,3,3-trifluoropropene to the step of producing 2,3,3,3-tetrafluoropropene as a starting material.

10. The process according to claim 9, wherein the separation of 2,3,3,3-tetrafluoropropene from the products of the step of producing 2-chloro-3,3,3-trifluoropropene or from the products of the step of reheating the products of the step of producing 2-chloro-3,3,3-trifluoropropene is performed by distillation.

* * * * *